United States Patent [19]

Inlow et al.

[11] Patent Number: 5,156,964
[45] Date of Patent: Oct. 20, 1992

[54] METHODS FOR ADAPTING CELLS FOR INCREASED PRODUCT PRODUCTION THROUGH EXPOSURE TO AMMONIA

[75] Inventors: Duane Inlow; Brian Maiorella, both of Oakland; Andrea E. Shauger, Albany, all of Calif.

[73] Assignee: Cetus Corporation, Emeryville, Calif.

[21] Appl. No.: 824,694

[22] Filed: Jan. 21, 1992

Related U.S. Application Data

[63] Continuation of Ser. No. 568,406, Aug. 16, 1990, abandoned.

[51] Int. Cl.$^5$ .............. C12N 15/00; C12N 5/00; C12N 5/02; C07K 3/00
[52] U.S. Cl. .............. 435/172.1; 435/240.1; 435/240.2; 435/240.27; 435/240.3; 435/240.31; 530/350; 530/388.1; 530/388.15; 530/865
[58] Field of Search .............. 435/172.1, 240.1, 240.2, 435/240.27, 240.3, 240.31; 530/387, 350

[56] References Cited
U.S. PATENT DOCUMENTS
4,724,206 2/1988 Rupp et al. .............. 435/68

OTHER PUBLICATIONS
Beeraj R. D. Can. J. Microbiol. 29:563-569, 1983.
Miller et al. Bioprocess Engineering, 3:3 pp. 113-122, 1988.
Pedersen et al. Annals of the New York Academy of Sciences vol. 506, Biochemical Engineering V, 1987.

Primary Examiner—David L. Lacey
Assistant Examiner—Gian P. Wang
Attorney, Agent, or Firm—James M. Heslin; Gregory J. Giotta; Wean Khing Wong

[57] ABSTRACT

This invention is in the field of cell and/or tissue culture. In particular, this invention relates to methods which adapt cells to a desired phenotype by exposing the cells to high levels of ammonia in culture, and subsequently transferring the adapted cells to a new culture medium in which there is no initial level of ammonia or the initial level of ammonia is below the level to which cells have been exposed to during the adaptation process. In this new culture medium, the adapted cells express the desired phenotype of growing to a higher viable cell density, and/or remaining viable for a longer period of time, and/or producing more of a desired cell product than their non-adapted counterparts grown in the same medium. This invention includes the adapted cells produced thereby and their cell products.

12 Claims, 3 Drawing Sheets

METHODS FOR ADAPTING CELLS FOR INCREASED PRODUCT PRODUCTION THROUGH EXPOSURE TO AMMONIA

This is a continuation of application Ser. No. 07/568,406, filed Aug. 16, 1990, now abandoned.

FIELD OF THE INVENTION

This invention is in the field of cell and/or tissue culture. In particular, this invention relates to methods which adapt cells to a desired phenotype by exposing said cells to high levels of ammonia in culture. This invention includes the adapted cells produced thereby and their cell products.

BACKGROUND OF THE INVENTION

In the production of cell culture derived products, low maximum viable cell density and product expression levels result in high production costs. Birch, J. R., et al., "Large Scale Production of Monoclonal Antibodies" presented at Biotech '85 USA conference, Washington, D.C., Oct. 21-23, 1985. In traditional cell culture, cell growth and product expression are often limited due to the use of non-optimal culture media. Applicants have shown that product expression can be increased several fold by using media which contain synergistic combinations of nutrients (copending U.S. patent application "Cell Culture Medium for Enhanced Cell Growth, Culture Longevity and Product Expression", to Howarth, W., et al., U.S. Ser. No. 248,634 now abandoned). However, even in these superior media conditions, growth and product expression can still be optimized by further improving growth and product expression and thereby reducing production costs. The invention presented by the current patent application provides means for such optimization.

Ammonia has been shown to affect cells in culture in two ways. First, ammonia is a waste product of cellular metabolism which is toxic to the cells. Second, applicants have demonstrated a solute stress effect of ammonia whereby the per cell expression rate of secreted protein products can be increased in the presence of ammonia in the culture medium (but at the expense of a decrease in cell growth rate and/or maximum viable cell density) (U.S. patent application "Method of Increasing Product Expression through Solute Stress", to Maiorella, B., et al., U.S. Ser. No. 122,015, filed on Nov. 18, 1987 now abandoned).

In culture solution, ammonia can exist in the form of ammonia or ammonium ions. As used in this patent application, the word "ammonia" includes the above two forms. Ammonia is a normal waste product of amino acid metabolism and in particular of glutamine metabolism (Haussinger, D., Sies, H., *Glutamine Metabolism in Mammalian Tissue*, Springer Verlag, 1984; McKeehan, W. L. "Glycolysis, Glutaminolysis and Cell Proliferation", *Cell Biology International Reports*, 6(7):635– 650, 1982; Reuveny, S., et al., 1986, *J. Immunol. Methods*, 66: 53-59). It is also produced by the spontaneous degradation of glutamine in the medium (Ozturk, S. S., et al., 1990, *Biotechnol. Progress*, 6:121-128). When left to accumulate, it can reach a toxic level in the culture and cause the cessation of cell growth and eventually cell death (Holley, R. W., et al., 1978, PNAS (USA), 75(4):1864-1866). It can also adversely affect production of cell products (Reuveny, S., et al., 1986, "Factors Affecting Cell Growth and Monoclonal Antibody Production in Stirred Reactors", *J. Immun. Methods*, 86:53-59).

The solute stress effect of ammonia can be observed when ammonia is added in such concentration, at least above the concentration found optimal for cell growth but less than that which causes culture death. The per cell rate of product expression and/or the culture longevity of cells under solute stress is comparatively greater than in the absence of added ammonia.

Attempts at overcoming the toxic effect of ammonia have centered around the removal of ammonia from cell culture. For example, by means of continuous replenishment of the culture medium, computer controlled glutamine level (Glacken, M. W., et al., 1986, "Reduction of Waste Product Excretion via Nutrient Control", *Biotech. Bioeng.*, 28:1376-1389), and continuous perfusion (Reuveny, S., et al., 1986, "Comparision of Cell Propagation Methods for their Effect on Monoclonal Antibody Yield in Fermentors", *J. Immun. Methods*, 86:61-69). Some researchers have also advocated minimizing the concentration of glutamine present in the culture by adapting the culture to grow in the absence of glutamine and with glutamic acid as an alternate substrate (Griffiths, J. B., et al., 1967, "The Uptake of Amino Acids by Mouse Cells During Growth in Batch Culture and Chemostat Culture, the Influence of Cell Growth Rate", *Proc. Roy. Soc. B.*, 168:421-438). In other cases, glutamine is slowly added throughout the time course of the culture to maintain a relatively constant low concentration of glutamine (Glacken, M. W., et al., 1986, "Reduction of Waste Product Excretion via Nutrient Control: Possible Strategies for Maximizing Product and Cell Yields on Serum in Cultures of Mammalian Cells", *Biotechnol. Bioeng.*, 28:1376-1389). However, these methods have proved unsatisfactory, due to for example, the complicated machinery entailed in the regulatory system.

Recently, investigations had been conducted regarding the toxicity of ammonia to mammalian cells in chemostat culture medium. These investigations employed the addition of ammonia and lactate to the medium in pulses and step changes (Miller, W. M., *A Kinetic Analysis of Hybridoma Growth & Metabolism*, U.C. Berkeley (Doctoral Dissertation, 1987); Miller, W. M., et al., 1988, *Bioprocess Engineering*, "Transient responses of hybridoma cells to lactate and ammonia pulse and step changes in continuous culture.") Miller et al., had also presented abstracts, "Transient and steady-state responses in continuous hybridoma culture—monoclonal antibody preparation", *Abst. Pap. Am. Chem. Soc.*, MBTD 128, 1988; and "Kinetic analysis of transient responses in continuous hybridoma suspension— effect of culture medium composition" *Abst. Pap. Am. Chem. Soc.*, MBTB 149, 1987.

The inhibitory ammonia concentration varies markedly between cell lines (Miller, W. M., et al., Bioprocess Engineering, supra). For example, the growth of mouse 3T3 cells was inhibited by less than 1 mM added ammonium chloride, whereas the growth of human HL-60 cells was inhibited at about 9 mM added ammonium chloride. Id. Miller et al., observed that a mouse hybridoma cell line AB2-143.2 gradually developed a tolerance to ammonia added in the feed to a continuous culture. It was originally observed that 5 mM of ammonia inhibited the growth of AB2-143.2 cell line. The cells were considered to have adapted to 8.2 mM of ammonia in the feed stream when in the culture fed with 8.2 mM ammonia they grew to the same cell concentration as non-adapted cells grown in medium without added ammonia (*A Kinetic Analysis of Hybridoma Growth & Metabolism*, supra. at p. 126; and Miller, W. M, et al., *Bioprocess Engineering*, supra). No data was presented on product expression. Miller et al., did not demonstrate nor show how cells can be adapted to acquire a phenotype by being exposed to ammonia such that the adapted cells would grow to a higher cell density and/or produce more cell products, as compared to their non-adapted counterparts, when both are subsequently grown in a culture medium without an initial added ammonia or with added ammonia at a level lower than that which the cells have been exposed to during the adaptation process.

SUMMARY OF THE INVENTION

One aspect of the invention presents methods for adapting cells in the presence of high levels of ammonia in vitro.

Another aspect of the invention presents methods which adapt cells to a desired phenotype by exposing them to ammonia in culture at a level at or below their maximum tolerable level; then transferring the adapted cells to a culture medium in which there is no initial level of ammonia or the initial level of ammonia is below the level to which the cells have been exposed to; in the latter culture medium, the adapted cells express the desired phenotype, i.e., growth to higher viable cell density and/or increased culture longevity and/or production of more cell products than their non-adapted counterparts grown in the same medium. The adaptation can be carried out in any number of ways, including the chemostat step change and batch culture passage methods.

Another aspect of the invention presents batch culture passage methods, which are non-step and non-pulse change methods, for adapting cells to express the desired phenotype in a cell culture system.

Another aspect of the invention presents a method for adapting cells to express the desired phenotype in a cell culture system, by means of passaging the cells into successive media containing ammonia at the initial maximum level, denoted A1, tolerated by non-adapted cells; continuing the passages until the cells can grow to a similar cell density and at a similar rate in the medium containing the A1 ammonia level as can the non-adapted cells in a medium without an initial level of ammonia.

Another aspect of the invention presents a method for adapting cells to the desired phenotype in a cell culture system, by means of passaging the cells into successive media containing ammonia at the initial maximum level, denoted A1, tolerated by non-adapted cells, continuing the passages until the cells can grow to a similar cell density and at a similar rate in a medium containing the A1 ammonia level as can the non-adapted cells in a medium without an initial level of ammonia; repeating the passages using increasing levels of ammonia, denoted A2, A3 etc., to obtain cells adapted in the A2, A3 etc., levels of ammonia.

Another aspect of the invention presents cells which have become adapted by culture in the presence of added ammonia to express the desired phenotype of growing to a higher cell density and/or remaining viable for a longer period of time in a culture and/or producing more product than their non-adapted counterparts when both are grown in a medium in which there is no initial level of ammonia or the initial level of ammonia is below the level to which the cells have been exposed to during the adaptation process.

Another aspect of the invention presents cells which have become adapted to express the desired phenotype, and can be frozen for later use without losing their adaptation.

DETAILED DESCRIPTION OF THE INVENTION

Figure 1:
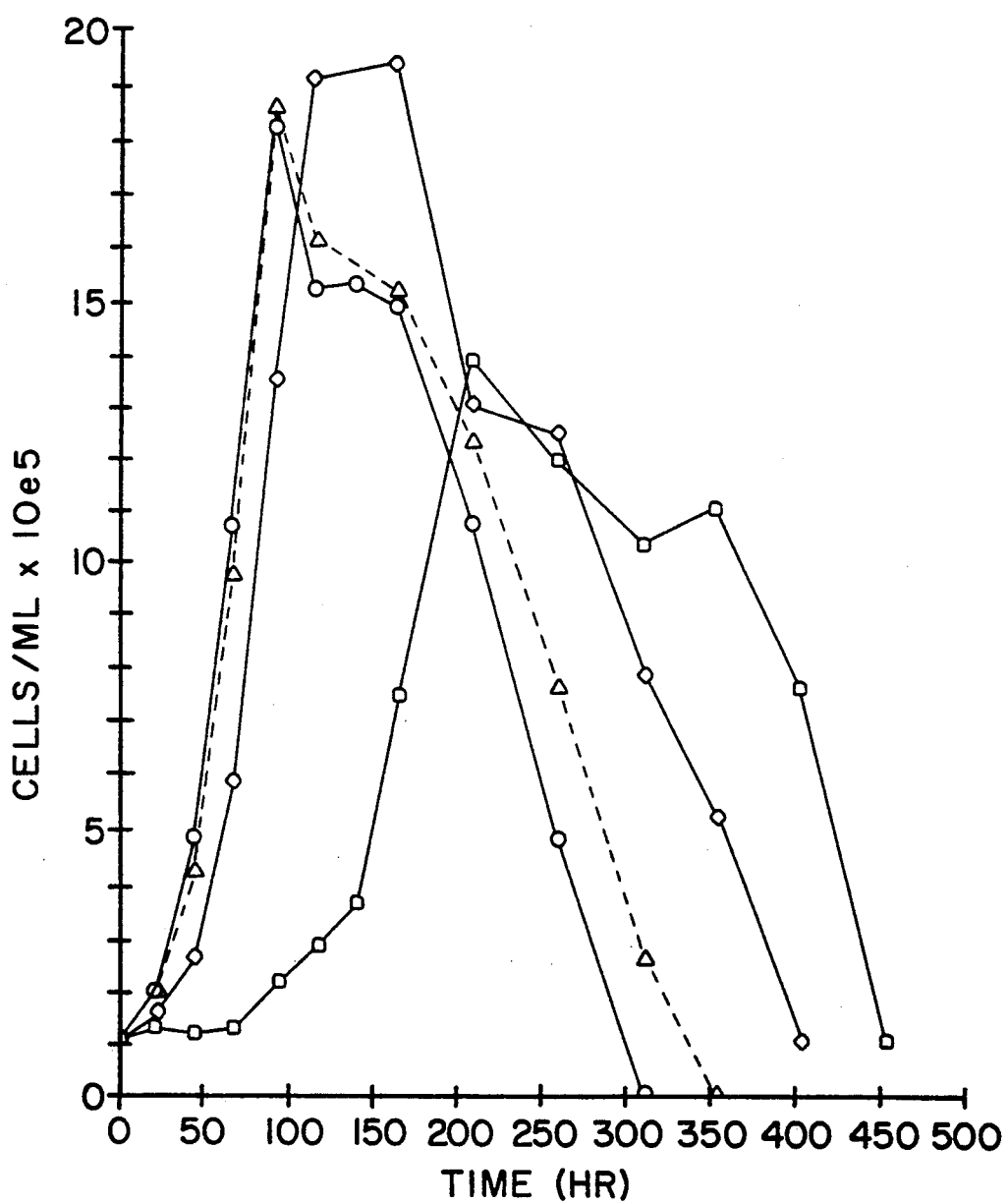
FIG. 1 shows the growth of T88 in DM21 with the addition of $NH_4Cl$:0, 2, 4, and 6 mM.

The invention described herein draws on previously published work and pending patent applications. By way of example, such work consists of scientific papers, patents or pending patent applications. All of these publications and applications, cited previously or below are hereby incorporated by reference.

The advantage of the present invention lies in the simplicity of its execution. This invention presents methods for adapting cells to express a desired phenotype by exposing the cells to ammonia in vitro. Further disclosed are cells and cell lines produced as a result of such adaptations.

The cells are adapted to express the desired phenotype by being exposed to a level of ammonia at or below their maximum tolerable level. This can be achieved by adding ammonia to the culture medium. The adaptation can be carried out in any methods which expose the cells for an adequate period of time to allow them to acquire the desired phenotype. For example, the adaptation may be carried out by the chemostat step change method (disclosed in the Miller et al. references cited above, hereinafter referred to as the step change method), or by the batch culture passage method disclosed in this patent application. Preferably, the cells are grown in a culture medium containing ammonia for a period of time adequate to allow them to adapt in the presence of ammonia. Compared to non-adapted cells, the adapted cells express the desired phenotype of growing to higher viable cell density, and/or longer viability, and/or producing more cell products when they are grown in a cell culture medium without an initial level of ammonia (i.e. no ammonia has been added to the culture medium before the cells are inoculated into the medium), or with an initial level of ammonia below that to which the cells have been exposed during the adaptation process. Preferably, the adapted cells are grown in culture media which contain nonlimiting levels of nutrients, thus allowing optimal cell growth. The preferred culture media are the culture media (with or without nutrient feeds and reagents) disclosed in pending U.S. Ser. No. 248,634, now abandoned filed Sep. 23, 1988, W. Howarth, et al., "Cell Culture Medium for Enhanced Cell Growth, Culture Longevity and Product Expression", which contain high level of glutamine and/or alanine. Further, preferably the adapted cells can be frozen for later use without losing their adaptation to ammonia.

The adaptation methods described herein are independent of the culture methods used. For example, they can be practiced in combination with the following culture methods: simple batch culture as in T-flasks or roller bottles (Glacken, M. W., et al., 1983, *Trends in Biotechnology*, 1(4):102–108) or simple batch suspension culture in stirred vessels (Phillips, A. W. et al., 1985, "Experience in the Cultivation of Mammalian Cells on the 8000 L Scale, "*Large-Scale Mammalian Cell Culture*, Academic Press, p. 87-95) or airlift vessels (Lambert, K. J. et al., 1987, "Production of Monoclonal Antibodies Using Large-Scale Cell Culture, " *Dev. Indust. Microbiology*, 27:101–106); continuous culture (Ray, N. G. et al., 1989, "Cultivation of Hybridoma Cells in Continuous Cultures: Kinetics of Growth and Product Formation" *Biotechnol. Bioeng.*, 33:724–730); hollow fiber reactors (Altshuler, G. L., et al., 1986, *Biotechnol Bioeng* 28:646–658); static maintenance reactors (Feder, J., et al., EPA 83870128.2, published Nov. 7, 1984); ceramic matrix reactors (Marcipar, A., et al., 1983, *Annals N.Y. Acad Sci.* 413:416–420); bead immobilized reactors (Nilsson, K., et al., 1983, *Nature*, 302:629–630); perfusion reactors (Feder, J., et al., 1985, *American Biotechnol Laboratory* III:24–36) and other culture methods as known in the art.

Having generally described the adaptation methods, the following provides the specific example of how the adaptation is achieved by means of the passage method. The method comprises adding ammonia to a cell culture medium to a concentration which inhibits, but does not completely abolish cell growth. This ammonia concentration is the initial maximum level of ammonia tolerated by the non-adapted cells, this ammonia level is hereinafter referred to as A1. The inhibition in cell growth may be seen, for example, in the reduction by day 3 (after inoculation) of viable cell density to about 20 to 50%, and preferably 30% in comparison to control culture (cells grown in medium without added ammonia). The cells are inoculated, preferably at about 1 to $1.5 \times 10^5$ viable cells/ml, into a fresh medium to which A1 level of ammonia has been added. The cells are allowed to grow for several generations, preferably to between about 3 to $10 \times 10^5$ viable cells/ml in this same culture medium. During this period, as is typical of normal batch culture, the ammonia level in the cell culture increases mainly due to glutamine metabolism. Next, the cells are inoculated into a fresh medium to which A1 level of ammonia has been added and again allowed to grow as before, these passages are repeated until the cells can tolerate the shock of being inoculated into a fresh medium containing ammonia at A1 level. The adaptation is shown by the increase in viable cell density, and/or longer viability, and/or increased in production of a desired cell product by the adapted as compared to the non-adapted cells when both are grown under the same conditions, preferably in media without an initial added ammonia or with an initial added ammonia level which is below the level to which the cells have been adapted to. It should be noted that the adapted cells can, in fact, tolerate more than the A1 level of ammonia, since during the culture period the ammonia level increases beyond A1 due to cellular metabolism and spontaneous degradation of glutamine found in culture media. Once the cells have become tolerant to inoculation into A1 level of ammonia, further adaptation of the cells in the presence of higher levels of ammonia can be continued by repeating the passages using higher levels of ammonia, denoted A2, A3 etc., to obtain cells adapted in the A2, A3 etc., levels of ammonia.

It would be appreciated by those skilled in the art that the minimum and maximum viable cell densities achievable by a cell culture are dependent on the particular cell line and culture medium used. Therefore, the viable cell densities for inoculation and prior to transfer to a fresh medium are similarly cell line and cell culture medium dependent. Thus, the numbers provided above are exemplary only. Those skilled in the art would be able to arrive at the appropriate viable cell densities by following the guidelines of: 1) inoculating the cells into the fresh culture medium at an initial viable cell density which would allow the cells to reach the exponential growth phase; and 2) transferring the cells to a fresh culture medium before they enter the stationary phase of growth. Exponential growth phase is the growth phase in which the viable cell number of the cell culture is increasing approximately exponentially. Stationary phase is the phase in a cell culture in which the viable cell density is relatively constant.

Similarly, the number of passages required for the adaptation in the presence of ammonia is also dependent on the cell line used. Approximately 3 to 30, and preferably 5 to 15 passages are generally required. Further, the various cell lines may differ in their tolerance of ammonia, therefore the maximum level of ammonia which they can tolerate in the adaptation described herein may differ. Thus, the maximum level of ammonia which could be tolerated and to which a particular cell line can be exposed to in order to acquire the desired phenotype could be higher or lower than the level shown in the example below. The methods described herein, however, are independent of the cell lines, culture methods and culture media used. The cell products may be of any variety. Thus, for example, the invention can be used for the production of monoclonal antibodies by hybridomas.

Using the above as a guide, those with ordinary skill in the art could adapt the chemostat step change method to use in place of the passage method to achieve the adaptation disclosed in this patent application. The following distinguish the passage, step change, and pulse change methods. The passage method differs from the prior art references, Miller, W. M., *A Kinetic Analysis of Hybridoma Growth & Metabolism*, supra.; Miller, W. M., et al., 1988, *Bioprocess Engineering*, supra.; Miller W. M., et al., *Abst. Pap. Am. Chem. Soc.*, MBTD 128 and 149, supra. Unlike the batch culture growth method used in this patent application, these references used continuous suspension culture growth method wherein fresh medium was continuously added to the cell culture reactor, with an equal volume of cell suspension being simultaneously removed. The pulse and step changes employed in the references also differ from the passage method disclosed in this patent application. In each of the passages disclosed in this patent application, the cells are inoculated into a culture medium containing an initial high level of ammonia, and allowed to continue growth in this medium wherein the ammonia level continues to slowly increase due to cellular metabolism and spontaneous degradation of principally glutamine. After a few generations of growth in this medium, the cells are inoculated into a fresh medium containing the same or higher level of ammonia, and the process repeated.

In contrast, the pulse change method is implemented by adding concentrated metabolite solution to the reactor, and the reactor contents are continuously replaced with fresh medium. Therefore, in the pulse change method, the concentration of the added metabolite sharply increases and then decreases and levels off within a relatively short period of time. On the other hand, the effects of a step change method are persistent because the metabolite concentration in the feed stream is also increased. Therefore, in the step change method, the metabolite concentration remains high and constant.

The present invention differs from the prior art in that the prior art does not subsequently grow the adapted cells in a culture medium without an initial level of ammonia or with an initial level of ammonia below that which the cells have been exposed to. Further, the prior art does not investigate whether in the latter medium, the adapted cells produce more cell products, have higher viable cell density, or longer viability period, than the non-adapted cells.

The following example illustrates one embodiment of the invention: adaptation using the passage method. Clearly, the example is not intended to be limiting upon the scope of the invention.

EXAMPLE 1

Adaptation of T88 to Ammonia-Containing Medium

The hybridoma T88 was adapted to express the desired phenotype by growing in media containing 5 mM ammonium chloride. Compared to non-adapted hybridomas, the adapted hybridomas expressed the desired phenotype of higher viable cell densities and increased production of IgM, when grown in a medium without an initial added level of ammonia.

A. Materials and Methods

This example used mammalian hybridoma T88 which produces human monoclonal antibodies T88 of the IgM class. The detailed description of the synthesis of hybridoma T88, including its fusion protocol, ELISAs and hybrid screening procedure, is disclosed in U.S. Ser. No. 057,763, now abandoned filed Jun. 3, 1987, entitled "GramNegative Bacterial Endotoxin Blocking Monoclonal Antibodies", by James W. Larrick, et al. Briefly, T88 is a trioma produced by somatic cell hybridization using a mouse x human parent hybrid cell line (designated F3B6) and Epstein-Barr virus (EBV)-transformed human splenocytes.

Shake flask and fermentor cultures of T88 were grown in DM21. DM21 had negligible ammonia. However, unlike the typical culture medium, DM21 contains high level of glutamine content. Due to the high level of glutamine in DM21, cells grown in DM21 typically produce about 8 mM or above of ammonia. As grown under conditions described in this example, T88 cell culture typically produces about 10 to 30 mM of ammonia by the time of harvesting of the antibodies. The composition of DM21 is presented below in Table 1.

TABLE 1

| Composition of DM21 | |
|---|---|
| Component | Mg/L |
| 1. Arginine | 500.0000 |
| 2. Arginine.HCL | 42.0000 |
| 3. Asparagine | 178.4000 |
| 4. Aspartate | 60.0000 |
| 5. Glutamate | 60.0000 |
| 6. Glycine | 70.0000 |
| 7. Histidine | 107.5000 |
| 8. Histidine.HCL.H$_2$O | 21.0000 |
| 9. Hydroxyproline | 10.0000 |
| 10. Isoleucine | 327.4000 |
| 11. Leucine | 327.4000 |

TABLE 1-continued

| Composition of DM21 | |
|---|---|
| Component | Mg/L |
| 12. Lysine.HCL | 343.1000 |
| 13. Methionine | 122.5000 |
| 14. Phenylalanine | 140.5000 |
| 15. Proline | 60.0000 |
| 16. Serine | 136.0000 |
| 17. Threonine | 207.6000 |
| 18. Tryptophan | 110.5000 |
| 19. Tyrosine.2Na.2H$_2$O | 216.0000 |
| 20. Valine | 206.8000 |
| 21. pAminobenzoic Acid | 0.5000 |
| 22. Biotin | 0.1000 |
| 23. Ca Pantothenate | 2.1250 |
| 24. Folic Acid | 2.5000 |
| 25. Nicotinamide | 2.5000 |
| 26. Pyridoxal.HCL | 2.0000 |
| 27. Pyridoxine.HCL | 0.5000 |
| 28. Riboflavin | 0.3000 |
| 29. Thiamine.HCL | 2.5000 |
| 30. Vitamin B12 | 0.0025 |
| 31. Ca(NO$_3$)$_2$.H$_2$O | 50.0000 |
| 32. KCl | 400.0000 |
| 33. MgSO$_4$.7H$_2$O | 150.0000 |
| 34. NaCl | 5000.0000 |
| 35. NaH$_2$PO$_4$.H$_2$O | 830.0000 |
| 36. Na$_2$HPO$_4$.7H$_2$O | 360.0000 |
| 37. Glucose | 5250.0000 |
| 38. Glutathione (Reduced) | 0.5000 |
| 39. Na Pyruvate | 110.0000 |
| 40. NaHCO$_3$ | 2850.0000 |
| 41. Phenol Red | 10.0000 |
| 42. Choline Chloride | 43.5000 |
| 43. Inositol | 41.0000 |
| 44. FeCl$_3$.6H$_2$O | 2.7000 |
| 45. Fe(NO$_3$)$_3$.9H$_2$O | 0.0500 |
| 46. (NH$_4$)$_6$Mo$_7$O$_{24}$ | 0.1000 |
| 47. CoCl$_2$.6H$_2$O | 0.1000 |
| 48. CuCl$_2$.2H$_2$O | 0.1000 |
| 49. MnCl$_2$.4H$_2$O | 0.1000 |
| 50. ZnCl$_2$ | 0.1000 |
| 51. Na$_2$SeO$_3$ | 0.0200 |
| 52. Na Citrate.2H$_2$O | 294.1000 |
| 53. HEPES | 2979.0000 |
| 54. Cystine | 199.0000 |
| 55. Ethanolamine | 10.0000 |
| 56. Monothioglycerol | 1.0000 |
| 57. Glycerol | 200.0000 |
| 58. Insulin | 5.0000 |
| 59. Transferrin | 5.0000 |
| 60. Selenous Acid | 0.0050 |
| 61. Pluronic Polyol F68 | 1000.0000 |
| 62. Glutamine | (8–40 mM) |

In the following experiments, the cells were inoculated into fresh DM21 culture medium containing 5.25 g/l and 8 mM of glucose and glutamine respectively. Throughout the life of the cell culture, glucose and glutamine were fed so as not to become depleted. Glucose (2 g/l) was added on days 3 and 5. Glutamine (4 mM) was added every second day starting on day 3 until the culture was dead.

To determine the upper limit in the initial NH$_4$Cl tolerance, the cells were inoculated at 1 to 1.5×10$^5$ viable cells/ml into shake flasks containing DM21 to which NH$_4$Cl were added in the following amounts: 0, 2, 5, 10, and 15 mM. The viable cell density of the cultures was monitored. It was observed that cell growth was slight or nonexistent for the shake flasks containing 5, 10, and 15 mM NH$_4$Cl. The shake flask containing 5 mM NH$_4$Cl had less than 50% viable cells/ml compared to the control culture (grown in medium without added NH$_4$Cl) on day 3. The cultures with 10 to 15 mM ammonia did not survive the lag phase.

With the above information, a second experiment was conducted in which the hybridomas T88 were inoculated at 1 to 1.5×10⁵ viable cells/ml into DM21 with 0, 2, 4, and 6 mM of NH₄Cl respectively. The 6 mM culture was passaged on day 6 into fresh DM21 containing 5 mM NH₄Cl, because of the long lag phase exhibited in the 6 mM culture. This 5 mM culture was then serially passaged into fresh media with 5 mM NH₄Cl. After 7 passages, these adapted cells were compared with non-adapted cells. The adapted and non-adapted cells were inoculated into three flasks each of DM21 with the addition of 0, 5, and 10 mM NH₄Cl.

B. Results and Discussion

FIG. 1 shows the growth curves and final IgM titers for non-adapted T88 cultures grown in DM21 with the addition of 0, 2, 4, and 6 mM NH₄Cl. Ammonia toxicity was seen in the increased lag phase of the cells and the lower viable cell densities. At 6 mM ammonia the lag phase extended to day 6 and the growth curve was lower and longer than for the control culture. The longer stationary phase seen here has been associated in other experiments with increased IgM production. For these cultures, a 39% increase in IgM production was seen with the addition of 6 mM ammonia: 278 mg/l for the 6 mM culture: 200 mg/l for the control.

Figure 2:
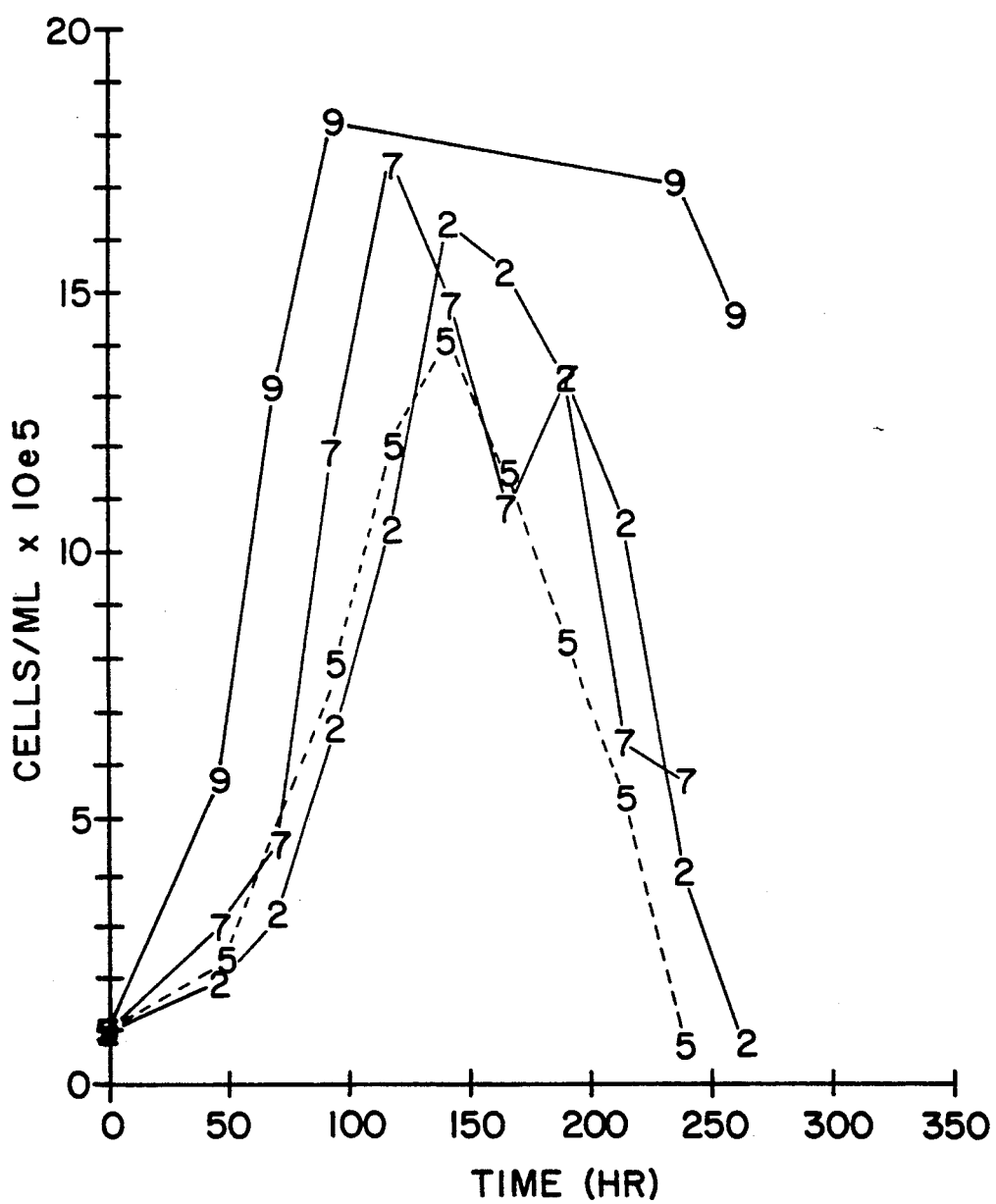
FIG. 2 shows the serial passages of T88 in DM21 plus 5 mM $NH_4Cl$.

Cells grown in 6 mM NH₄Cl were then re-inoculated into medium containing 5 mM NH₄Cl and repeatedly passaged, as described above. FIG. 2 shows growth and IgM titers (day 10 unless noted otherwise) for some of these serial passages. The lag phase was reduced with increased passages and the cells did not, in general, show the increase in the duration of stationary phase seen with passage 1 (compare to the 6 mM NH₄Cl curve in FIG. 1). Notably, passage 9 remained at high viable cell densities for a longer period of time than normally seen with non-adapted T88.

Figure 3:
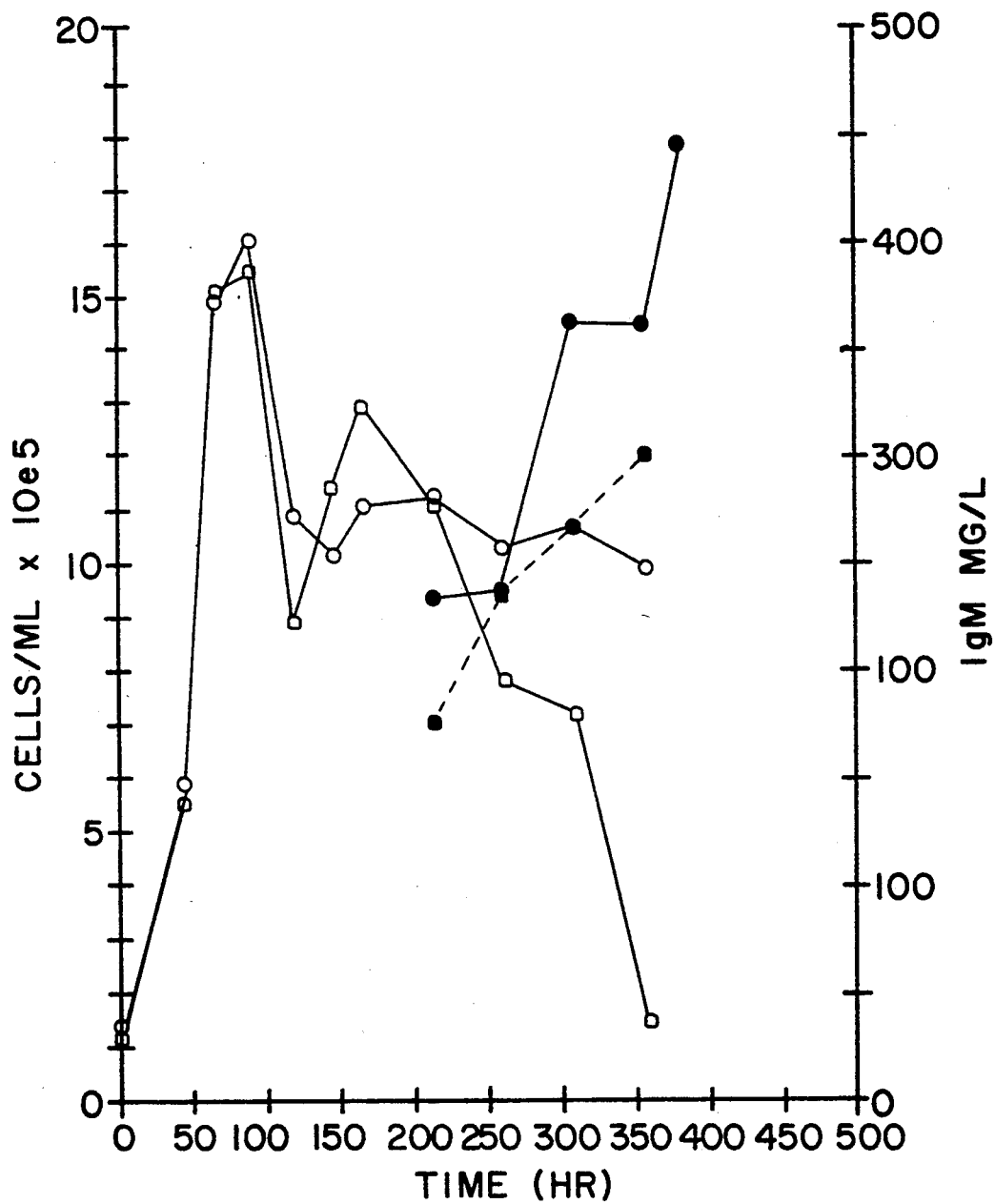
FIG. 3 shows a comparison of growth and IgM production for adapted versus non-adapted cells in DM21 without added $NH_4Cl$.

After 7 passages in the ammonia-containing medium, cells at 1 to 1.5×10⁵ viable cells/ml were inoculated into medium with 0, 5, and 10 mM NH₄Cl. Parallel cultures were started using non-adapted cells. Cultures containing 10 mM ammonia did not survive more than several days. FIG. 3 shows the growth and IgM curves for the adapted and non-adapted cells in DM21 without added NH₄Cl. Adapted cells showed higher viable cell densities at the end of stationary phase than non-adapted cells. These cells also produced more IgM: 446 mg/l as compared to the 300 mg/l for the non-adapted cells, which was an increase of 49%.

In summary, T88 has been adapted to express the desired phenotype by being grown in DM21 to which 5 mM of NH₄Cl had been added. When grown in normal medium, these adapted cells then expressed the desired phenotype of maintaining higher viable cell densities and producing more IgM than non-adapted cells.

Further, starting with their adaptation at 5 mM, the method disclosed herein had been used to expose hybridomas T88 to 10 mM of NH₄Cl. However, it was observed that when T88 cells which had been exposed to 10 mM of ammonia were grown in a medium without added NH₄Cl, they produced less antibody, exhibited lower maximum cell density, and shorter survival period than non-adapted T88 grown under the same conditions.

As shown in the examples above, it is not necessarily true that if the cells have been adapted to increasing higher levels of ammonia, beyond the maximum that they can initially tolerate (which is beyond A1), that they would then perform best in media without added ammonia, as compared to cells adapted to lesser levels of ammonia and non-adapted cells. As shown in the examples, T88 adapted to 5 mM of NH₄Cl performed better than non-adapted cells in medium without added NH₄Cl, whereas T88 exposed to 10 mM of NH₄Cl performed worse than non-adapted cells. Utilizing the invention disclosed herein, those skilled in the art can determine and adapt each cell line to the appropriate ammonia level tolerated by the particular cell line in question.

Without wishing to be bound to any theory, it is hypothesized that after the adapted cells have passed through several passages in non-ammonia containing media, they may revert to having the same viability and productivity as non-adapted cells.

The present invention has been described with reference to specific embodiments. However, this application is intended to cover those changes and substitutions which may be made by those skilled in the art without departing from the spirit and the scope of the appended claims. Further, various modifications of the invention in addition to those shown and described herein apparent to those skilled in the art from the preceding description are considered to fall within the scope of the appended claims.

We claim:

1. A method for adapting mammalian cells to one or more of the following desired phenotypes comprising growth to a higher viable cell density, longer viability, or production of a greater amount of a desired cell product compared to their non-adapted cell counterparts, when both are grown in a medium without an initial level of ammonia or with an initial level of ammonia which is below the level to which the adapted cells have been exposed during the adaptation, wherein the adaptation comprises the steps of:
   a) inoculating the cells into a cell culture medium to which ammonia has been added at a level, designated A1, at or below the maximum level of ammonia which the cells can tolerate;
   b) growing the cells in the medium of step a) for a period of time; and
   c) repeating steps a) and b) using said A1 level of ammonia at least once and for a number of times which is sufficient for the cells to express the desired phenotype(s).

2. The method of claim 1, wherein the level of ammonia designated A1 is the ammonia level which inhibits, but does not completely abolish cell growth.

3. The method of claim 2, wherein the maximum level of ammonia that the cells can tolerate is the ammonia level at which cell growth is inhibited to about 20% to 50% around day 3 after inoculation as compared to cells grown in a medium without added ammonia.

4. The method of claim 2, wherein the cells are inoculated into the medium of step a) before they enter stationary phase of growth and they are inoculated at an initial viable cell density which would allow the cells to reach exponential growth phase; and the cells in step b) are grown for several generations.

5. The method of claim 2, wherein the cells are inoculated into the medium of step a) at about 1 to 1.5×10⁵ viable cells/ml, and in step b) the cells are grown to between about 3 to 10×10⁵ viable cells/ml.

6. The method of claim 2, wherein steps a) and b) are repeated about 3 to 30 times.

7. The method of claim 2, wherein the steps are repeated to further adapt the cells in the presence of a higher level of ammonia, designated A2.

8. The method of claim 7, wherein the maximum level of ammonia that the cells can tolerate is the ammonia level at which cell growth is inhibited to about 20% to 50% on around day 3 after inoculation as compared to cells grown in a medium without added ammonia.

9. The method of claim 7, wherein the cells are inoculated into the medium of step a) at about 1 to $1.5 \times 10^5$ viable cells/ml, and in step b) the cells are grown to between about 3 to $10 \times 10^5$ viable cells/ml.

10. A method for adapting cells to one or more of the following desired phenotypes comprising growth to a higher viable cell density, longer viability, or production of a greater amount of a desired cell product compared to their non-adapted cell counterparts, when both are grown in a medium without an initial level of ammonia or with an initial level of ammonia which is below the level to which the adapted cells have been exposed during the adaptation, wherein the adaptation comprises the steps of:

a) inoculating the cells, at about 1 to $1.5 \times 10^5$ viable cells/ml, into a cell culture medium having an initial level of ammonia, designated A1, wherein A1 is the level of ammonia at which cell growth is inhibited to about 20% to 50% at about day 3 after inoculation as compared to cells grown in a medium without an initial level of ammonia;

b) growing the cells in the medium of step a) until about 3 to $10 \times 10^5$ viable cells/ml are grown; and c) repeating steps a) and b) using A1 level of ammonia until the cells express the desired phenotype(s).

11. The method claim 10, wherein the steps are repeated to adapt the cells in the presence of a higher level of ammonia, designated A2.

12. A method for adapting mammalian cells to one or more of the following desired phenotypes comprising growth to a higher viable cell density, longer viability, or production of a greater amount of a desired cell product compared to their non-adapted cell counterparts, when both are grown in a medium without an initial level of ammonia or with an initial level of ammonia which is below the level to which the adapted cells have been exposed during the adaptation, wherein the adaptation comprises the steps of:

(a) inoculating the cells into a cell culture medium to which ammonia has been added at a level, designated A1, at or below the maximum level of ammonia which the cells can tolerate;

(b) growing the cells continuously in the medium of step (a) for a period of time sufficient for the cells to express the desired phenotype(s).

* * * * *